United States Patent [19]
Rogers

[11] Patent Number: 6,152,873
[45] Date of Patent: Nov. 28, 2000

[54] OTOSCOPE FOR EXAMINATION AND TREATMENT OF THE EAR

[75] Inventor: George R. Rogers, Danbury, Conn.

[73] Assignee: Boehringer Ingelheim Pharmaceuticals, Inc., Ridgefield, Conn.

[21] Appl. No.: 09/260,627

[22] Filed: Mar. 1, 1999

[51] Int. Cl.[7] .................................................. A61B 1/267
[52] U.S. Cl. .......................... 600/200; 600/199; 600/187; 600/156
[58] Field of Search ................................ 600/200, 199, 600/187, 153, 156

[56] References Cited

U.S. PATENT DOCUMENTS

| | | | |
|---|---|---|---|
| 3,848,587 | 11/1974 | McDonald | 128/9 |
| 4,785,796 | 11/1988 | Mattson | 128/9 |
| 5,665,094 | 9/1997 | Goldenberg | 606/109 |
| 5,674,183 | 10/1997 | Adachi | 600/158 |
| 5,688,224 | 11/1997 | Forkey et al. | 600/200 |

*Primary Examiner*—Linda C. M. Dvorak
*Assistant Examiner*—Jocelyn Debra Ram
*Attorney, Agent, or Firm*—R. P. Raymond; M-E M. Devlin, Esq.; A. R. Stempel, Esq.

[57] ABSTRACT

An otoscope having (a) a gripping body; (b) a hollow ear speculum, having an outer end adapted to be placed in the ear canal of a patient, said ear speculum being connected to a top end of the gripping body; (c) a viewing port connected to the top end of said gripping body to provide a line of sight through the ear speculum; (d) a light source which is directed through said ear speculum; and (e) a dispenser which is integral with said otoscope for ejecting medicament through the ear speculum.

7 Claims, 7 Drawing Sheets

OTOSCOPE FOR EXAMINATION AND TREATMENT OF THE EAR

BACKGROUND OF THE INVENTION

The present invention provides a novel otoscope, which may be used for concurrent examination and administration of medication to the ear.

Otoscopes are well known devices that physicians and otologists use in the inspection of the ear. The typical otoscope has an elongated tubular body, a light source, a viewing means and an ear speculum. Some models, such as the preferred embodiment of U.S. Pat. No. 4,006,738, have a fiber optic light conducting element which allows the light source to be located in a position which is remote from the lens, providing a more compact design and more precise control of the manner in which light is applied for viewing the ear canal. A device, which is intended to deliver medication to the ear canal, is described in U.S. Pat. No. 5,176,654. That device comprises a fluid reservoir attached to a pump-type dispenser which is actuated to deliver fluid to the ear canal through a delivery tip. The delivery tip is enlarged in order to restrict the depth to which it may be inserted into the ear canal of a patient.

The present applicant has devised a novel otoscope, which is adapted to allow examination of the ear canal with concurrent administration of medication, without the need to remove the otoscope from the ear canal.

SUMMARY OF THE INVENTION

An otoscope is disclosed which comprises:
(a) a gripping body;
(b) a hollow ear speculum, having an outer end adapted to be placed in the ear canal of a patient, said ear speculum being connected to a top end of said elongated tubular body;
(c) viewing means connected to said top end of said elongated tubular body to provide a line of sight through said ear speculum;
(d) a light source which is directed through said ear speculum; dispensing means which is integral with said otoscope for ejecting medicament through said ear speculum.

It is an object of the invention to provide an otoscope which allows for concurrent examination and administration of a medicament to the ear canal.

It is also an object of the invention to provide an otoscope which has an integral dispenser for medicaments that may be actuated concurrently with the examination of the ear canal.

It is also an object of the invention to provide an otoscope for dispensing medicaments with an integral dispenser concurrently with the examination of the ear wherein the dispenser is located within the tubular handle of the otoscope.

It is also an object of the invention to provide an otoscope for dispensing medicaments with an integral dispenser concurrently with the examination of the ear, the dispenser being located on the outside of the tubular handle of the otoscope.

These and other objects of the invention will become apparent from a review of the appended specification.

DETAILED DESCRIPTION OF THE INVENTION

The invention provides an otoscope which is adapted for examination of the ear canal and concurrent administration of medication. The medication may be administered without the need to remove the otoscope from the ear canal.

The otoscope of the invention permits the examining physician to immediately dispense medication in response to a visual examination of the ear canal by activating dispensing means that are mounted internally or externally on the otoscope. The dispensing means may be a manual pump means that delivers medication by manual actuation or an aerosol control means that causes a metered dose of medication to be delivered to the ear canal from an aerosol container of medication that is provided with a metered dose delivery valve.

The type of medication may be selected in accordance with the particular problem that is expected to be encountered. In the case of otitis externa, antibiotic-antiinflammatory medicaments may be dispensed such as those which are described in U.S. Pat. No. 5,843,930, which is incorporated by reference. In addition, local anesthetics may also be administered alone or in combination with antibiotic or antiinflammatory medicaments in cases where severe pain is present or it is necessary to carry out procedures which will cause pain of discomfort such as myringotomy with or without insertion of tympanostomy tubes. "OTOMIZE" is a brand of commercial ear spray that may be administered using the otoscope of the invention.

Figure 1:
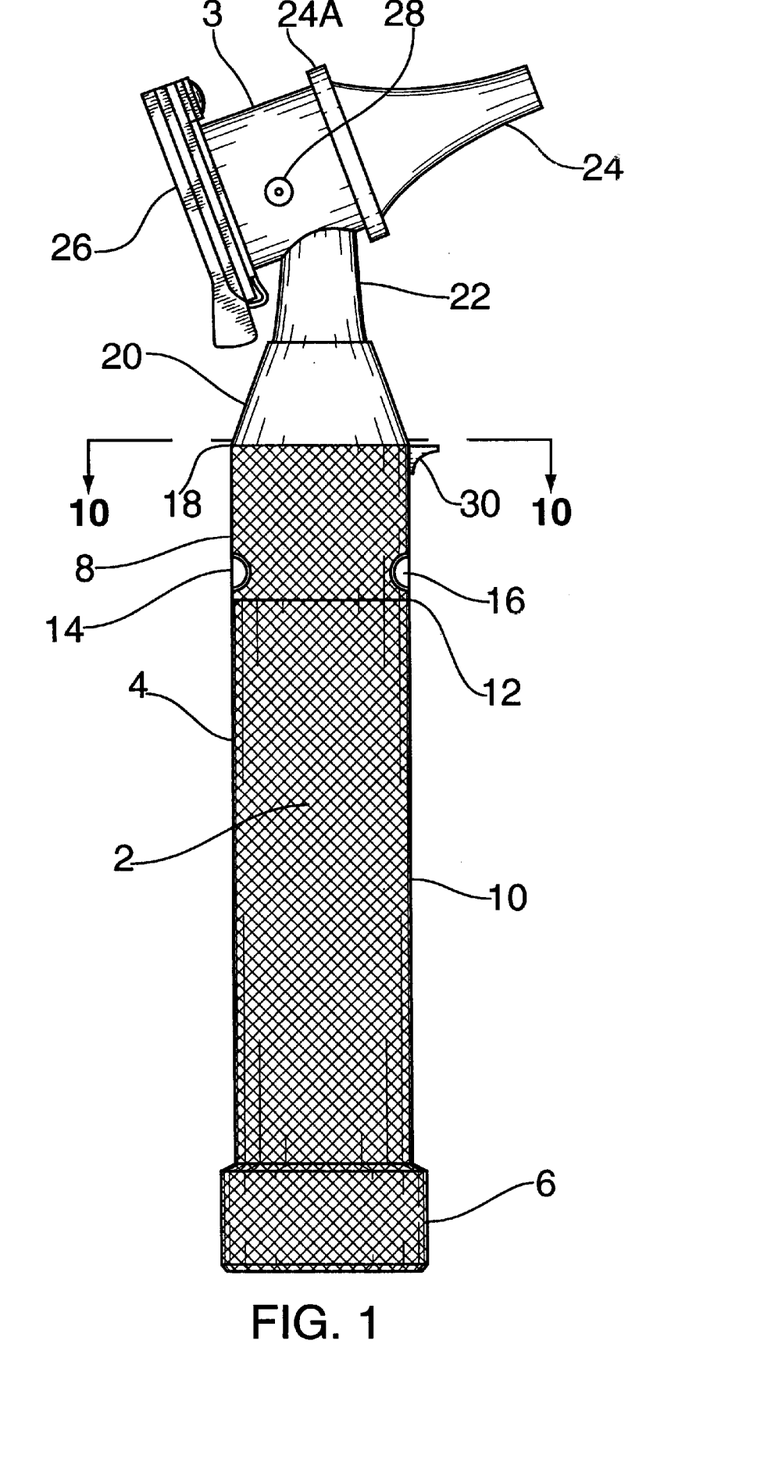
FIG. 1 is a side elevation view of the assembled device of the invention.

As best seen in FIG. 1, the exterior of otoscope 2 comprises a gripping barrel 4 which is an elongated tubular body, having a knurled surface which facilitates the holding of the otoscope in one hand. The otoscope may be made of a high performance-engineering thermoplastic or of a metal such as stainless steel. Metal is preferred as it is more durable and facilitates the internal wiring of the light source. The gripping barrel 4 has a bottom cap 6 which is threaded or friction fitted onto the gripping body 4 to provide access to the interior of the hollow inside cavity of the gripping barrel 4 for purposes of the insertion and removal of a battery (not shown in this FIG. 1). The battery could be disposable or re-chargeable. The gripping barrel 4 of the otoscope 2 comprises an upper portion 8 and a lower portion 10 which are joined at joint 12. The upper and lower portions may be threaded together, held by friction or secured by release buttons 14 and 16 which are spring mounted on the lower portion 10 of the gripping barrel 4. When the springs of buttons 14 and 16 are compressed, upper portion 8 may be slidably disengaged from lower portion 10. The upper end 18 of the upper portion 8 is connected to a frustoconical section 20 which is connected to truncated neck element 22 which is connected at it upper end to hollow head 3.

Hollow head 3 is sized to engage ear speculum 24 with a friction fit, which permits removal of the speculum for cleaning, or for mounting a different size speculum, i.e., a pediatric sized speculum. The speculum could be disposable or re-usable. The ear speculum has a generally sloped frustroconical shape as shown in FIG. 1 and a smooth surface that permits insertion of the ear speculum into the ear canal to a limited depth without injuring the ear. A flange 24A is provided on the end of the speculum, which engages head 3 in order to provide a gripping surface for removal and reattachment of the ear speculum to the head 3. Optionally, head 3 is provided with a magnifying or non-magnifying lens and/or filter assembly 26 which permits glare free magnified viewing of the ear canal through the speculum when the speculum is inserted into the ear. A vent hole 28 is provided in the head 3 which is sized to permit the user of the novel otoscope to employ pressure to deliver medicament to the ear canal without applying pressure to the tympanic membrane. An actuator handle 30 is preferably provided in the front of the gripping barrel 4 to permit finger actuation of the pump or aerosol valve in order to administer a dose of a medicament to the ear canal.

Figure 2:
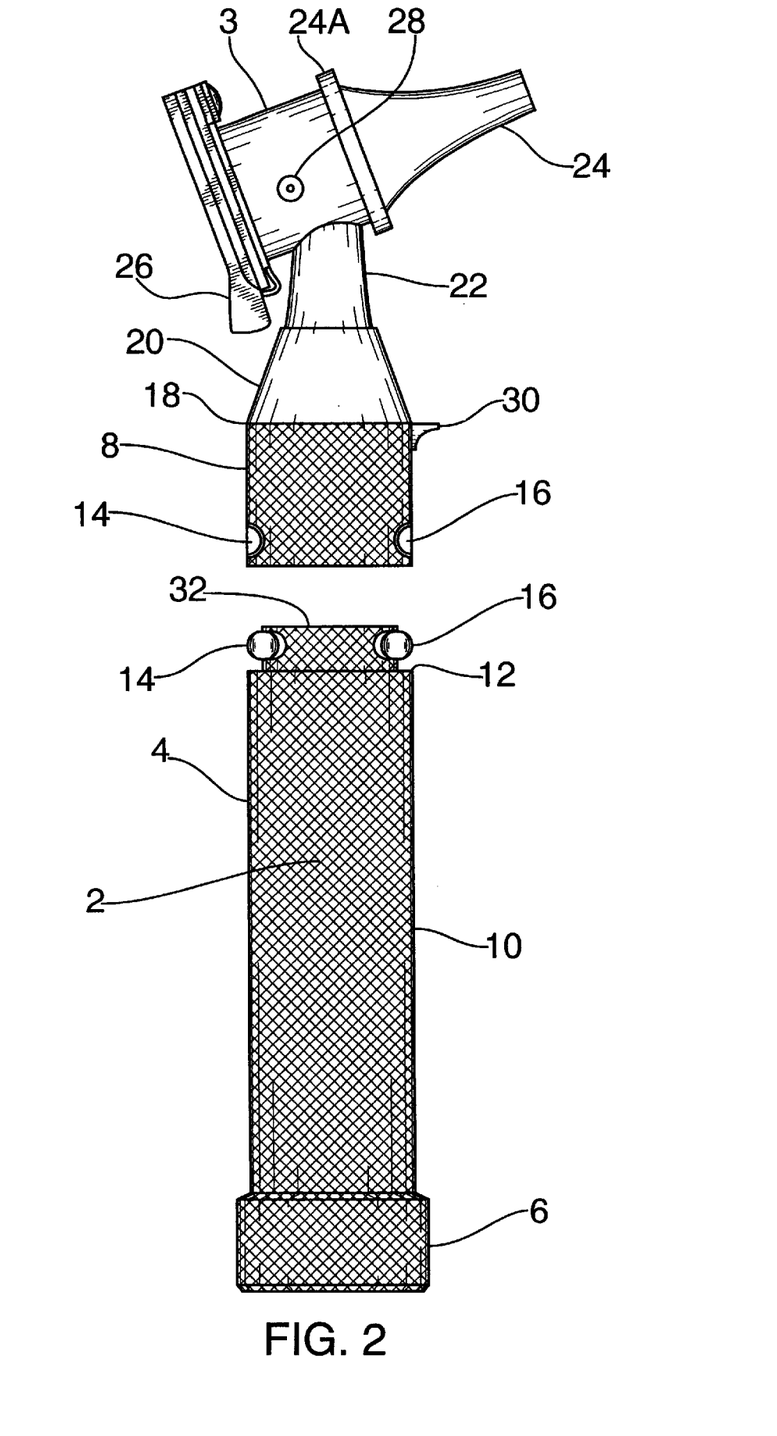
FIG. 2 is a side elevation view of the partially disassembled device of the invention.

The otoscope of the invention is shown in FIG. 2 in a disassembled form with upper portion 8 and a lower portion 10 separated at joint 12. Joint 12 is adjacent to a turned down section 32 which is sized to engage the inner surface of upper portion 8 to provide lateral stability and to control the depth of insertion when the upper portion 8 and lower portion 10 are joined together.

Figure 3:
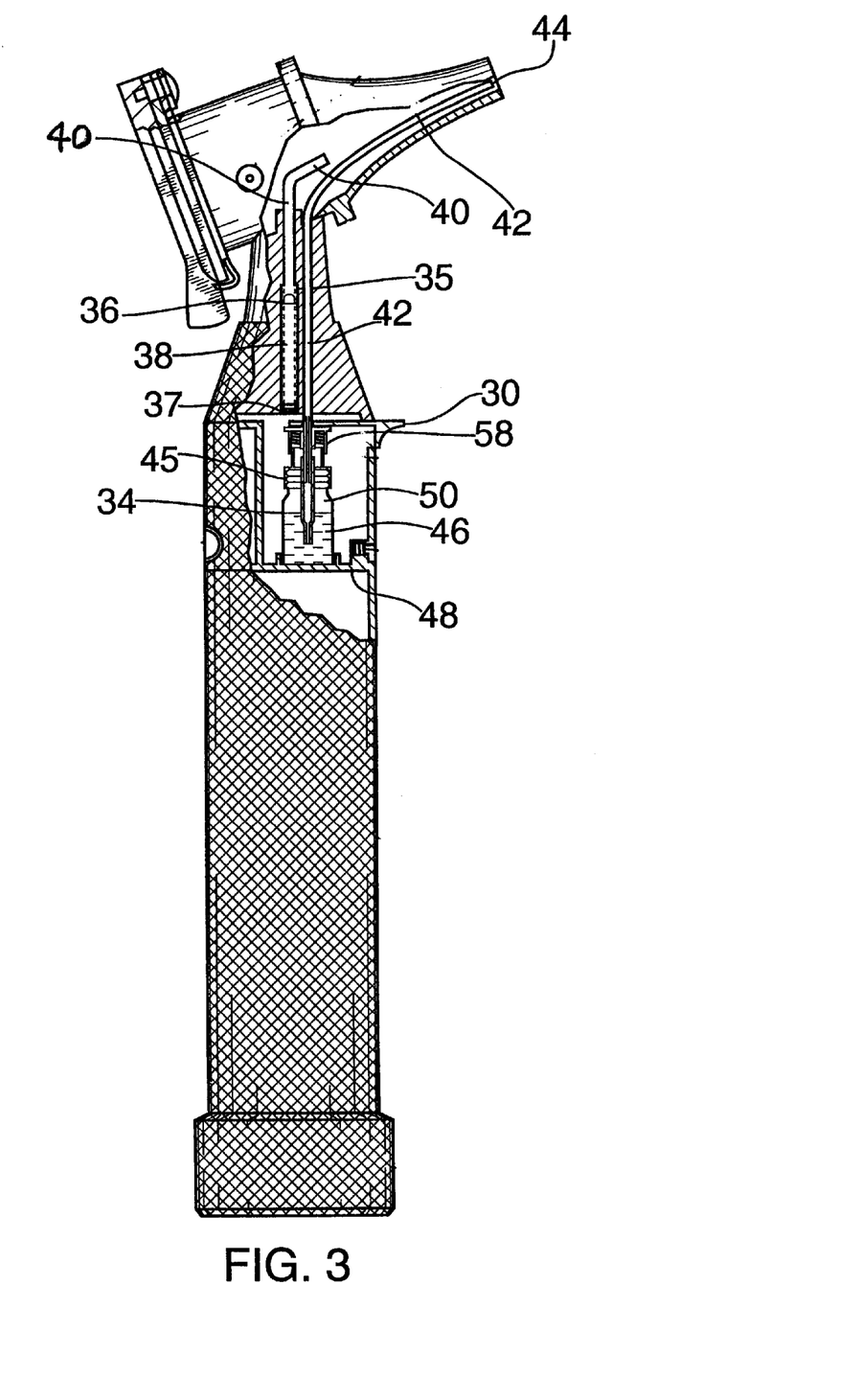
FIG. 3 is a partial cutaway view of a side elevation view of the invention showing an internally mounted medicament holder.

The internally mounted medicament dispenser and light emitting means are best seen in FIG. 3. The light emitting means is preferably a battery powered lamp 36 which is mounted in lamp assembly 35 at the top of lamp housing 38 in communication with fiber optic bundle 40. Contact points 37 are provided at the bottom of lamp housing 38 to connect to wires (not shown) which are connected to a power source. Spray tube 42 is connected to spray nozzle 44 to provide a means for the medicament 46 in medicament housing 34 to be administered through the end of the ear speculum. The top of the medicament housing 34 is covered with screw top 45 having a centrally located orifice through which spray tube 42 is passed. The medicament is preferably a liquid solution or suspension, i.e., in a formulation that can be absorbed. The medicament housing 34 is mounted on an internal platform 48. Inside of the medicament housing 34 is an air space 50 which is pressurizable with air that is pumped in by pump element 58 by depressing actuator 30. As actuator 30 is depressed, the air inside the medicament housing is compressed and the medicament is forced through spray tube 42.

Figure 4:
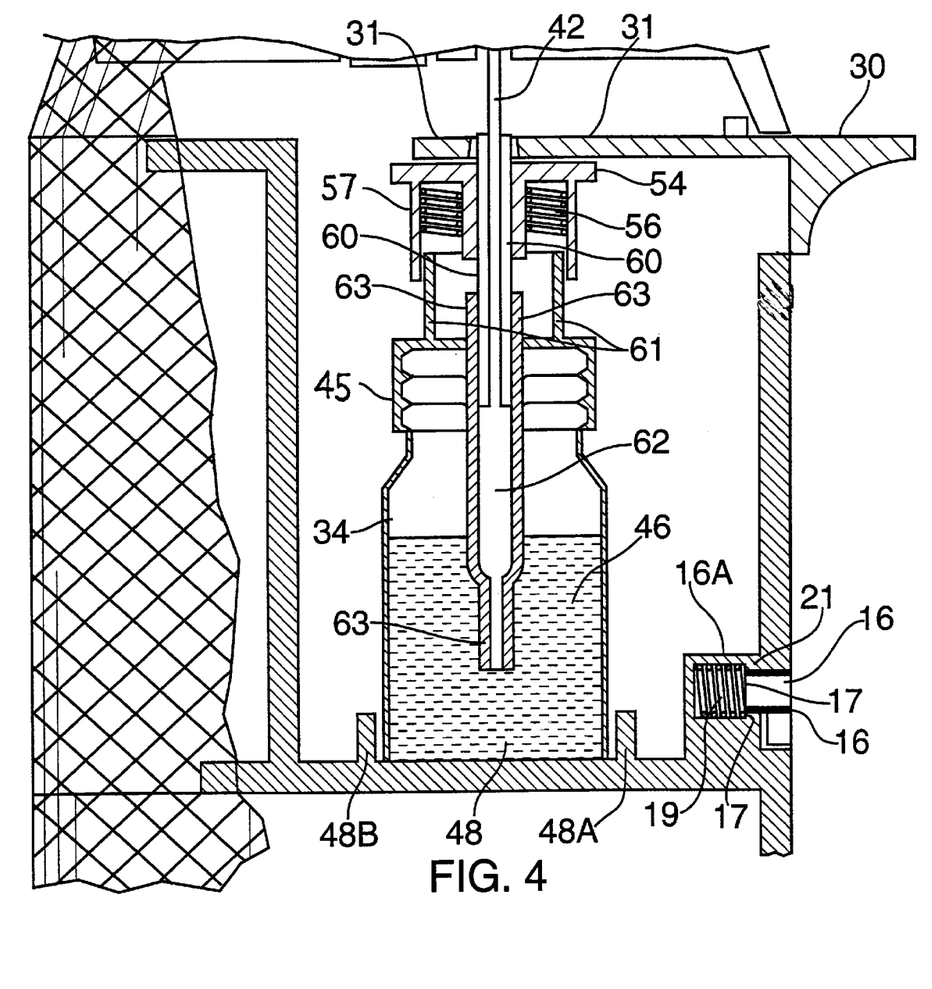
FIG. 4 is an enlarged view of the medicament holder and pump device which is shown in FIG. 3.

A preferred embodiment of a medicament dispenser is shown in FIG. 4 in cross section. The medicament dispenser has a pump head 54, return spring 56, internal pump supports 60 and external pump supports 57. Exterior wall supports 61 control the side to side movement of the pump head 54 as it is depressed to initiate the pumping action. Stop element 63 provides a means to control the depth to which the pump head 54 may be depressed and thus limits the amount of pressure that is applied to the ear canal through spray tube 42 into spray nozzle 44 (shown in FIG. 3). Screw cap 45 is placed on top of the medicament housing 34. A centrally located metered chamber tube 62 is submerged in medicament 46 with constricted tube segment 63. The internal platform 48 has a circular retaining well which is shown in section in FIG. 4 with right side section 48A and left side section 48B. Actuator 30 is connected to actuator arm 31 which engages pump head 54. Release button 16 is held in spring housing 16A with inner flange 17 that prevents the button from being ejected by the expansion of spring 19. When spring 19 is compressed by pushing button 16 below the level of side wall 21, the locking action of the button is neutralized, and the upper and lower section of the otoscope may be separated.

Figures 5, 6, 7:
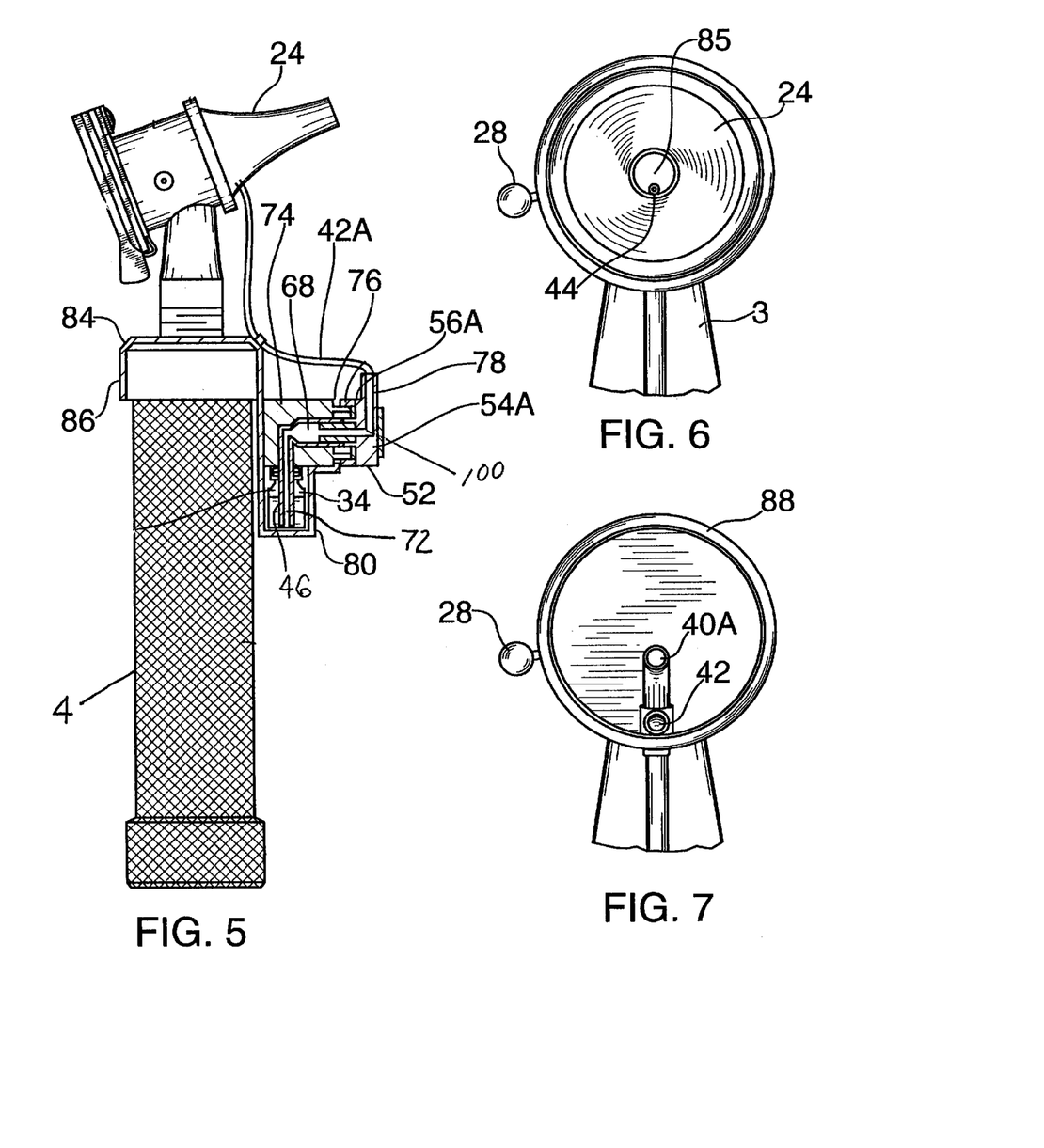
FIG. 5 is a side elevation of the device of the invention with a partial cutaway view of the medicament holder which is mounted on the outside of the device of the invention.
FIG. 6 is a front view of the ear speculum which is a part of the device of the invention.
FIG. 7 is a front view of the head of device of the invention.

FIG. 5 discloses an otoscope of the invention in which the medicament housing 34 and associated pump means is mounted on the outside of the gripping body 4 of the otoscope. This configuration of a dispensing means may be used to retrofit an ordinary otoscope with a medicament housing to provide an otoscope according to the present invention. The dispensing means comprises a medicament housing is attached to the gripping body 4 by bracket 80 which holds the medicament housing 34 in a fixed relation to the gripping body 4. The upper portion 84 of bracket 80 has a circular shaped housing which fits on the top of the gripping body 4 by means of a circular opening (not shown) and a skirt section 86 which circumferentially engages and grips the gripping body 4.

A spray tube 42A connects the medicament housing to the spray nozzle (not shown) which is internally attached to the end of the ear speculum 24 as shown in FIG. 3. The medicament dispenser in FIG. 5 has a manual pump actuator 54A and a spring 56A. When the actuator is depressed, chamber 68 is pressurized which causes medicament 46 to be ejected through dip tube 72 into spray tube 42A. Valve body 74 provides a housing member for chamber 68 and a stop mean 76 for the lower base of pump actuator means 54A. Spray tube 42A is fitted into the side of pump actuator at inlet port 78 and is connected to an opening 100 in the central axis of the pump actuator means 54A that communicates with chamber 68.

FIG. 6 is a front view of the ear speculum 24 which shows open ear insertion end 85 and the spray tube nozzle 44. FIG. 7 is a front view of the head 3 of the otoscope with the ear speculum removed. Facing edge 88 is the part of the head 3 that engages ear speculum 24.

Pressure relief opening 28 is positioned on the left side (when viewed from the front) of head 3. The end of the fiber optic bundle 40A is shown in close proximity to a section through spray tube 42.

Figure 8:
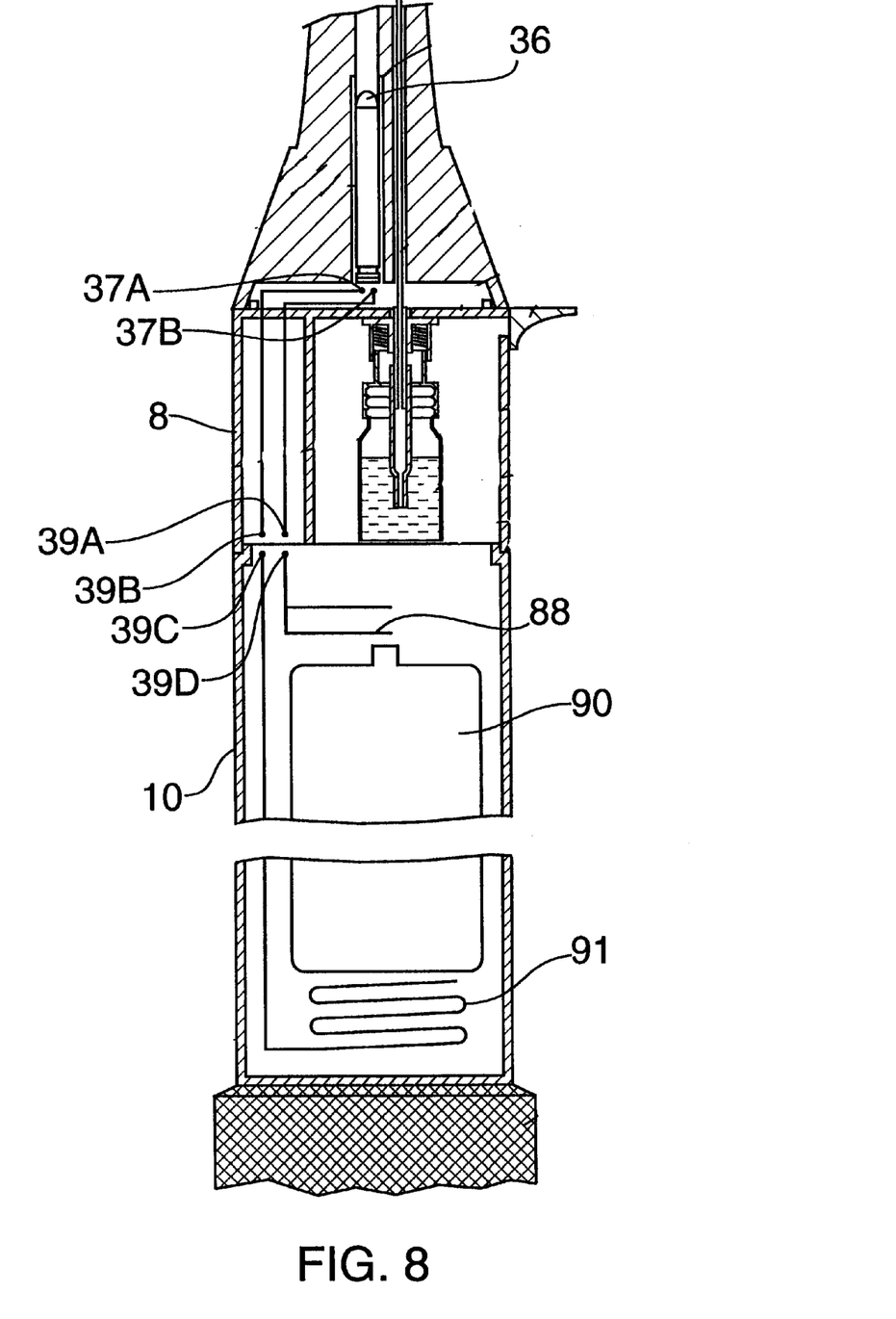
FIG. 8 is a partial cutaway view of a side elevation view of the invention showing an internally mounted medicament holder, the electrical circuit and battery.

FIG. 8 is a partial cross-section through the tubular body of the otoscope of the invention. The battery 90 is held in place by lower spring 91 and upper contact element 88. The electric contacts 39A and 39B are positioned against electrical contacts 39C and 39D to provide electrical continuity when upper portion 8 and lower portion 10 are connected to one another. The circuit to the lamp 36 is completed when a switch (37A and 37B) is closed which brings electric current to lamp 36.

Figure 9:
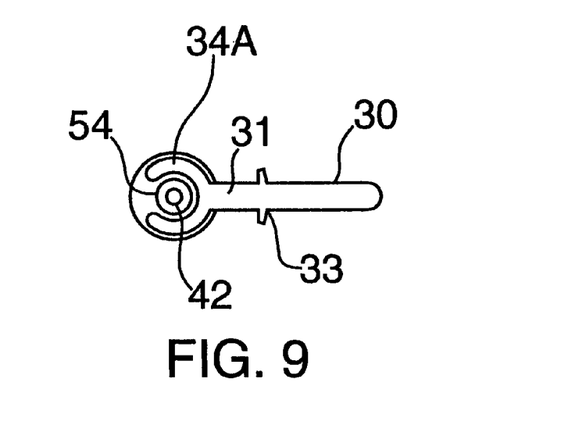
FIG. 9 is a top view of the actuator element which contacts the dispenser pump on the medicament holder.

FIG. 9 is a top view of the actuator 30 and actuator arm 31 which shows actuator support element 33. The actuator arm 31 has a "C" shaped end 34A which is placed on top of pump head 54. Spray tube 42 passes upwardly through the central portion of the pump head 54.

Figure 10:
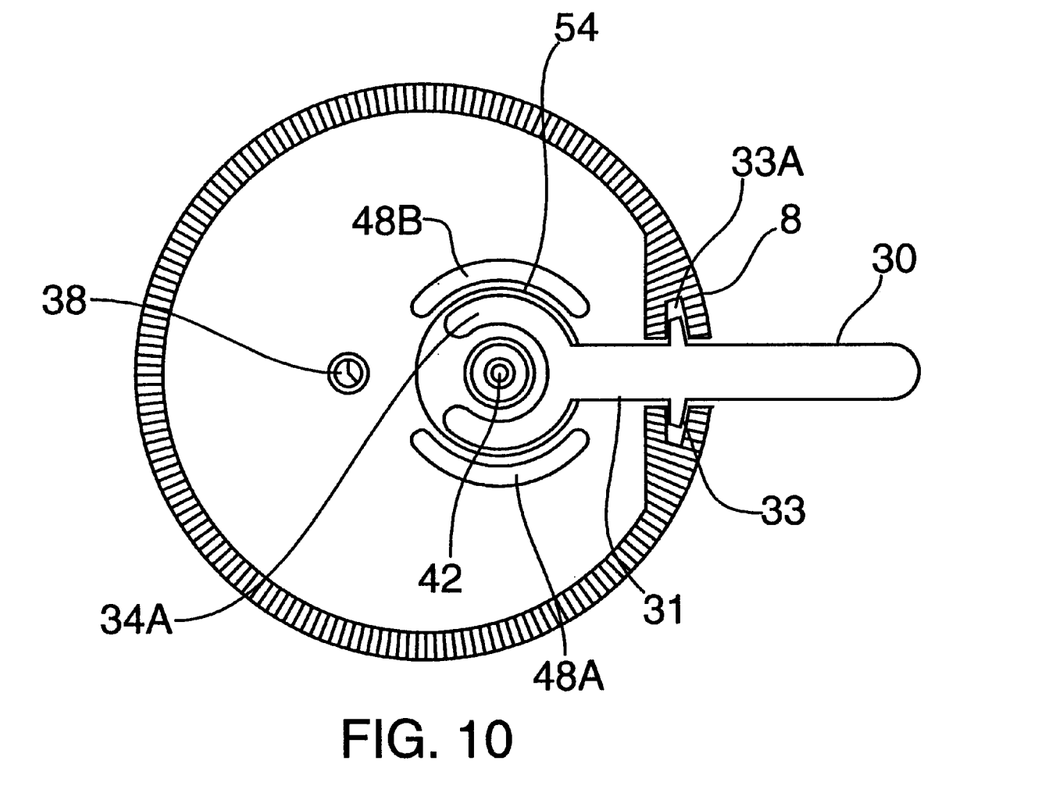
FIG. 10 is a cross section of FIG. 1 along 10—10 looking from top to bottom of the otoscope which shows the actuator element of the dispenser mounted on the dispenser pump.

FIG. 10 is a sectional view through FIG. 1 along line 10—10. Actuator support element 33 of actuator arm 31 is placed in a slot 33A in the side wall of upper portion 8 to allow the actuator arm 31 to be moved downwards to actuate a pump or aerosol element.

The foregoing description of a preferred embodiment of the invention has been presented for purposes of illustration and description. It is not intended to be exhaustive or to limit the invention to the precise form disclosed. Obvious modifications or variations are possible in light of the above teachings. All such obvious modifications and variations are intended to be within the scope of the appended claims.

What is claimed is:

1. An otoscope comprising:
   (a) a gripping body;
   (b) a hollow ear speculum, having an outer end adapted to be placed in the ear canal of a patient, said ear speculum being connected to a top end of said gripping body;
   (c) viewing means connected to said top end of said gripping body to provide a line of sight through said ear speculum;
   (d) a light source which is directed through said ear speculum; and
   (e) dispensing means which is integral with said otoscope for ejecting medicament through said ear speculum, and which is mounted externally on the gripping body of said otoscope.

2. An otoscope as defined in claim 1 wherein the dispensing means comprises an aerosol container.

3. An otoscope as defined in claim 1 wherein the dispensing means comprises a pump, a spray tube and a spray nozzle.

4. An otoscope as defined in claim 1 wherein the dispensing means is controlled by an actuator that is mounted in an opening of said gripping body.

5. A dispensing means for external mounting on an otoscope, said dispensing means comprising a bracket which holds a medicament housing in close proximity to the gripping body of an otoscope, said bracket comprising an upper portion having a circular shape which is adapted to fit on the top of the gripping body of an otoscope by means of a circular opening, said dispensing means having a skirt section on said upper portion for circumferentially engaging and gripping the gripping body of an otoscope during use.

6. A dispensing means for an otoscope as defined in claim 5 further comprising pump means in said medicament housing which is connected to a spray tube which connects said pump to a spray nozzle which is mounted in the open ear insertion end of a speculum of an otoscope.

7. An otoscope comprising:
   (a) a gripping body which comprises an upper portion and a lower portion which may be separated;
   (b) a hollow ear speculum, having an outer end adapted to be placed in the ear canal of a patient, said ear speculum being connected to a top end of said elongated tubular body;
   (c) magnifying viewing means connected to said top end of said elongated tubular body to provide a line of sight through said ear speculum;
   (d) a fiber optic light element which is directed through said ear speculum to project light through said speculum; and
   (e) dispensing means which are integral with said otoscope for ejecting medicament through said ear speculum, said dispensing means comprising a manual pump connected to a spray tube which connected to a spray nozzle that is mounted at the open insertion end of said speculum.

* * * * *